US009987011B2

(12) United States Patent
Williams et al.

(10) Patent No.: US 9,987,011 B2
(45) Date of Patent: Jun. 5, 2018

(54) SURGICAL FASTENER APPLYING APPARATUS

(71) Applicant: Covidien LP, Mansfield, MA (US)

(72) Inventors: Justin Williams, Southbury, CT (US); Christopher Penna, Guilford, CT (US); Paul Scirica, Huntington, CT (US); David Racenet, Killingworth, CT (US)

(73) Assignee: Covidien LP, Mansfield, MA (US)

(*) Notice: Subject to any disclaimer, the term of this patent is extended or adjusted under 35 U.S.C. 154(b) by 505 days.

(21) Appl. No.: 14/623,009

(22) Filed: Feb. 16, 2015

(65) Prior Publication Data
US 2015/0157323 A1 Jun. 11, 2015

Related U.S. Application Data

(63) Continuation of application No. 13/442,273, filed on Apr. 9, 2012, now Pat. No. 8,998,061, which is a
(Continued)

(51) Int. Cl.
*A61B 17/04* (2006.01)
*A61B 17/10* (2006.01)
(Continued)

(52) U.S. Cl.
CPC .......... *A61B 17/105* (2013.01); *A61B 17/068* (2013.01); *A61B 17/0644* (2013.01);
(Continued)

(58) Field of Classification Search
CPC . A61B 17/068; A61B 17/105; A61B 17/1155; A61B 2017/07278
(Continued)

(56) References Cited

U.S. PATENT DOCUMENTS 3,939,828 A * 2/1976 Mohr .................... A61B 17/68
606/221
4,289,133 A 9/1981 Rothfuss
(Continued)

FOREIGN PATENT DOCUMENTS

EP 2110085 A2 10/2009
EP 2436318 A2 4/2012
(Continued)

OTHER PUBLICATIONS

Japanese Office Action (with English Translation), dated Apr. 14, 2015, corresponding to Japanese Patent Application No. 2011-195041; 9 total pages.
(Continued)

*Primary Examiner* — Robert Long

(57) ABSTRACT

A surgical stapler is provided. The stapler includes a tubular body portion. A cartridge assembly is disposed at a distal end of the body portion for expelling an annular array of staples. Each of the staples of the annular array of staples has a generally bent backspan. An anvil member disposed at the distal end of the tubular body portion is positioned opposite the cartridge assembly to clinch the staples in tissue upon expulsion of the staples from the cartridge assembly. The anvil member has a corresponding annular array of staple forming buckets. Each of the buckets is configured to accommodate the generally bent configuration of the staples to facilitate formation thereof.

13 Claims, 13 Drawing Sheets

Related U.S. Application Data continuation-in-part of application No. 13/207,653, filed on Aug. 11, 2011, now Pat. No. 9,750,502.

(60) Provisional application No. 61/410,980, filed on Nov. 8, 2010, provisional application No. 61/388,788, filed on Oct. 1, 2010.

(51) Int. Cl.
*A61B 17/072* (2006.01)
*A61B 17/064* (2006.01)
*A61B 17/115* (2006.01)
*A61B 17/068* (2006.01)

(52) U.S. Cl.
CPC . *A61B 17/1155* (2013.01); *A61B 2017/07235* (2013.01); *A61B 2017/07264* (2013.01)

(58) Field of Classification Search
USPC .............................. 227/175.1–182.1; 606/142
See application file for complete search history.

(56) References Cited

U.S. PATENT DOCUMENTS

| | | | |
|---|---|---|---|
| 4,319,576 A | | 3/1982 | Rothfuss |
| 4,841,960 A | * | 6/1989 | Garner ............... A61B 17/0642 606/216 |
| 5,246,443 A | * | 9/1993 | Mai .................... A61B 17/0642 606/219 |
| 5,389,098 A | | 2/1995 | Tsuruta et al. |
| 5,489,058 A | * | 2/1996 | Plyley .................. A61B 17/064 227/176.1 |
| 5,497,933 A | | 3/1996 | DeFonzo et al. |
| 5,560,532 A | | 10/1996 | DeFonzo et al. |
| 5,816,471 A | | 10/1998 | Plyley et al. |
| 5,817,109 A | | 10/1998 | McGarry et al. |
| 5,839,639 A | | 11/1998 | Sauer et al. |
| 5,915,616 A | | 6/1999 | Viola et al. |
| 6,059,787 A | * | 5/2000 | Allen ................. A61B 17/0642 606/75 |
| 6,685,708 B2 | * | 2/2004 | Monassevitch .... A61B 17/0642 606/324 |
| 7,080,769 B2 | | 7/2006 | Vresh et al. |
| 7,234,624 B2 | | 6/2007 | Gresham et al. |
| 7,325,713 B2 | | 2/2008 | Aranyi |
| 7,351,258 B2 | * | 4/2008 | Ricotta ..................... A61F 2/07 623/1.23 |
| 7,398,907 B2 | | 7/2008 | Racenet et al. |
| 7,398,908 B2 | | 7/2008 | Holsten et al. |
| 7,407,075 B2 | | 8/2008 | Holsten et al. |
| 7,455,682 B2 | | 11/2008 | Viola |
| 7,611,038 B2 | | 11/2009 | Racenet et al. |
| 7,722,610 B2 | * | 5/2010 | Viola ................. A61B 17/0644 227/176.1 |
| 7,744,627 B2 | | 6/2010 | Orban, III et al. |
| 7,922,743 B2 | | 4/2011 | Heinrich et al. |
| 8,066,169 B2 | | 11/2011 | Viola |
| 8,113,406 B2 | | 2/2012 | Holsten et al. |
| 8,123,103 B2 | | 2/2012 | Milliman |
| 8,181,838 B2 | | 5/2012 | Milliman et al. |
| 8,186,556 B2 | * | 5/2012 | Viola ................. A61B 17/0644 227/177.1 |
| 8,231,041 B2 | * | 7/2012 | Marczyk ............. A61B 17/072 227/177.1 |
| 8,231,042 B2 | | 7/2012 | Hessler et al. |
| 8,328,063 B2 | | 12/2012 | Milliman et al. |
| 8,453,910 B2 | | 6/2013 | Bettuchi et al. |
| 8,453,911 B2 | | 6/2013 | Milliman et al. |
| 8,464,924 B2 | | 6/2013 | Gresham et al. |
| 8,511,533 B2 | | 8/2013 | Viola et al. |
| 8,540,132 B2 | | 9/2013 | Marczyk et al. |
| 8,596,514 B2 | * | 12/2013 | Miller ................. A61B 17/0642 128/898 |
| 8,806,973 B2 | | 8/2014 | Ross et al. |
| 8,998,061 B2 | | 4/2015 | Williams et al. |
| 2002/0185517 A1 | | 12/2002 | Vresh et al. |
| 2005/0067454 A1 | | 3/2005 | Vresh et al. |
| 2005/0245965 A1 | | 11/2005 | Orban, III et al. |
| 2007/0027473 A1 | | 2/2007 | Vresh et al. |
| 2007/0034666 A1 | | 2/2007 | Holsten et al. |
| 2007/0034667 A1 | * | 2/2007 | Holsten ............... A61B 17/072 227/176.1 |
| 2007/0034668 A1 | | 2/2007 | Holsten et al. |
| 2007/0057014 A1 | | 3/2007 | Whitman et al. |
| 2007/0131732 A1 | | 6/2007 | Holsten et al. |
| 2007/0181632 A1 | | 8/2007 | Milliman |
| 2007/0194079 A1 | | 8/2007 | Hueil et al. |
| 2008/0041918 A1 | | 2/2008 | Holsten et al. |
| 2008/0082124 A1 | * | 4/2008 | Hess .................... A61B 17/064 606/219 |
| 2009/0001121 A1 | | 1/2009 | Hess et al. |
| 2009/0026245 A1 | | 1/2009 | Holsten et al. |
| 2009/0255976 A1 | | 10/2009 | Marczyk et al. |
| 2009/0255978 A1 | | 10/2009 | Viola et al. |
| 2009/0277948 A1 | * | 11/2009 | Beardsley .......... A61B 17/0644 227/178.1 |
| 2009/0281554 A1 | | 11/2009 | Viola |
| 2009/0321496 A1 | | 12/2009 | Holsten et al. |
| 2010/0065607 A1 | | 3/2010 | Orban, III et al. |
| 2010/0127039 A1 | | 5/2010 | Hessler |
| 2010/0301098 A1 | | 12/2010 | Kostrzewski |
| 2011/0006100 A1 | | 1/2011 | Milliam |
| 2011/0042442 A1 | | 2/2011 | Viola et al. |
| 2011/0057016 A1 | | 3/2011 | Bettuchi |
| 2011/0089219 A1 | | 4/2011 | Hessler |
| 2011/0114701 A1 | | 5/2011 | Hessler |
| 2011/0130788 A1 | | 6/2011 | Orban, III et al. |
| 2012/0012641 A1 | | 1/2012 | Milliman et al. |
| 2012/0080483 A1 | | 4/2012 | Riestenberg et al. |
| 2012/0080492 A1 | | 4/2012 | Scirica et al. |
| 2012/0145768 A1 | | 6/2012 | Sorrentino et al. |
| 2012/0193398 A1 | | 8/2012 | Williams et al. |
| 2012/0228356 A1 | | 9/2012 | Milliman et al. |
| 2013/0030438 A1 | * | 1/2013 | Fox .................... A61B 17/0642 606/75 |
| 2013/0193192 A1 | | 8/2013 | Casasanta, Jr. et al. |
| 2015/0157323 A1 | | 6/2015 | Williams et al. |
| 2017/0360444 A1 | * | 12/2017 | Scirica ............... A61B 17/1155 |

FOREIGN PATENT DOCUMENTS

| | | |
|---|---|---|
| EP | 2649949 A1 | 10/2013 |
| EP | 2436318 B1 | 11/2016 |
| JP | 58-018510 | 7/1956 |
| JP | 34-5096 | 6/1959 |
| JP | 0006030945 A | 2/1994 |
| JP | 2008-512173 A | 4/2008 |
| JP | 2008114072 A | 5/2008 |
| JP | 2012-75872 A | 4/2012 |
| WO | 03/94747 A1 | 11/2003 |
| WO | 03094747 A1 | 11/2003 |
| WO | 2006/028314 A1 | 3/2006 |

OTHER PUBLICATIONS

European Communication dated May 11, 2015, corresponding to European Patent Application No. 13162779.6; 7 pages.
Chinese Office Action (With English Translation), dated Jul. 3, 2015, corresponding to Chinese Patent Application No. 201110274263.8; 15 total pages.
Japanese Notice of Final Rejection (with English Translation), dated Dec. 15, 2015, corresponding to Japanese Application No. 2011-195041, 7 total pages.
Chinese Office Action (with English translation), dated Jan. 5, 2016, corresponding to Chinese Application No. 201110274263.8; 18 total pages.
English translation of a microfilm of Japanese Utility Model Application No. 56-113942 (Japanese Laid-Open Utility Model Publication No. 58-018510), dated Jul. 31, 1981, corresponding to Japanese Application No. 2011-195041; 20 pages.

(56) References Cited

OTHER PUBLICATIONS

English translation of Japanese Publication for Opposition No. 34/5096, published Jun. 18, 1959, corresponding to Japanese Application No. 2011-195041, 6 pages.
English translation of Chinese Office Action, dated Mar. 2, 2016, corresponding to Chinese Application No. 201310121403.7; 11 pages.
European Communication dated May 31, 2016, corresponding to European Application No. 13162779.6; 6 pages.
Extended European Search Report corresponding to EP 11 25 0769.4, completed Jul. 23, 2013, and dated Jul. 30, 2013; (6 pp).
Extended European Search Report corresponding to EP 13 16 2779.6, completed Jun. 26, 2013, and dated Jul. 4, 2013; (9 pp).
U.S. Appl. No. 13/156,645, filed Jun. 9, 2011.
Chinese Second Office Action (With English Translation), dated Nov. 1, 2016, corresponding to Chinese Patent Application No. 201310121403.7; 8 total pages.
Japanese Office Action (with English translation), dated Nov. 21, 2016, corresponding to Japanese Application No. 2013-076726; 8 total pages.
European Communication issued May 11, 2015, corresponding to European Patent Application No. 13162779.6; 7 pages.
Chinese Office Action (With English Translation), dated Jun. 3, 2015, corresponding to Chinese Patent Application No. 201110274263.8; 15 total pages.
Canadian Office Action and Examination Report, dated Jul. 25, 2017, corresponding to Canadian Application No. 2.749,709; 5 total pages.
European Search Report, dated Jun. 23, 2017, corresponding to European Application No. 16201936.8; 13 pages.
Japanese Notice of Allowance with ENglish language Communication Summary Form, dated Jun. 27, 2017, corresponding to Japanese Application No. 2013-76726; 4 total pages.

* cited by examiner

SURGICAL FASTENER APPLYING APPARATUS

CROSS-REFERENCE TO RELATED APPLICATIONS

The present application is a continuation of U.S. patent application Ser. No. 13/442,273, filed on Apr. 9, 2012, which is a continuation-in-part of U.S. patent application Ser. No. 13/207,653, filed on Aug. 11, 2011, which claims benefit of U.S. Provisional Application No. 61/388,788, filed on Oct. 1, 2010, which claims benefit of U.S. Provisional Application No. 61/410,980, filed on Nov. 8, 2010, the entire contents of which is hereby incorporated by reference.

BACKGROUND

Technical Field

The present disclosure relates to surgical stapling instruments for applying surgical fasteners or staples to body tissue and, more particularly to surgical stapling instruments utilizing bent backspan staples and having a corresponding anvil including bent staple forming buckets.

Description of Related Art

Surgical stapling devices for applying an annular array of staples or fasteners to tissue are well known in the art. For example, such surgical stapling devices have particular utility in performing small bowel resection with end-to-end anastomosis. These devices, typically, include a staple pusher assembly or member and an anvil assembly or member at the distal end of the surgical stapling device. The anvil member is movable from a retracted configuration for positioning tissue between the anvil member and the cartridge assembly, to an advanced configuration for joining tissue, i.e., stapling the ends of a tubular organ in a body of the patient organ to be joined. One or more annular or circular arrays of fasteners, such as, for example, staples, is operably housed in the cartridge assembly. The anvil member includes one or more corresponding annular arrays of staple forming bucket members that clinch or form (e.g., in a "B" staple formation) the staples after the staples are expelled from the cartridge assembly. Generally, the staples include a straight backspan. As can be appreciated, the anvil bucket members and/or pushers associated with the cartridge assembly include a corresponding configuration, i.e., a generally straight configuration, to accommodate the straight backspan of the staples.

For a given staple pusher configuration configured for use with straight backspan staples, the number of staples that may be present in a given annular array of staples is limited by the length of the backspan of the staples and an inside and outside diameter of the cartridge assembly. Moreover, it is, typically, an inside annular array of the staples that determine the number of staples that may be present in each additional annular array of staples, e.g., middle and outer annular arrays, of the cartridge assembly. That is, an equal number of staples in each of the annular arrays is, typically, provided to allow for consistent overlap at a gap between each consecutive staple; a specific gap distance exists between each consecutive staple for each annular array of staples, with, typically, the smallest gap distance between each consecutive staple existing in the inner annular array and the gap distance between consecutive staples increasing from the inner annular array to the outer annular array(s). As a result thereof, the gap distances between consecutive staples in the inner and subsequent annular array(s) are unequal. These unequal gap distances are not conducive to obtaining a "tight" staple line. That is, an equal gap distance between consecutive staples in each annular array of staples may promote better healing of the stapled tissue, which, in turn, results in less bleeding and leakage at the stapled tissue line. Unfortunately, the length of the backspan of the aforementioned staples is limited by geometry from interfering with, i.e., extending into, the next row of staples. As a result thereof, subsequent to tissue being stapled with conventional surgical stapling devices, there exists a chance of bleeding and leakage occurring at the stapled tissue line, i.e., adjacent the area between consecutive staples in the annular array of staples in the outer annular array(s). Or, in certain instance, a compromised stapled tissue line being formed, which, in turn, may result in the stapled tissue separating.

SUMMARY

In an aspect of the present disclosure, a surgical stapler comprises: a tubular body portion; a cartridge assembly disposed at a distal end of the body portion for expelling an annular array of staples, each of the staples of the annular array of staples having legs and a generally bent or curved backspan; and an anvil member disposed at the distal end of the tubular body portion and positioned opposite the cartridge assembly to crimp the staples in tissue upon expulsion of the staples from the cartridge assembly, the anvil member having a corresponding annular array of staple forming buckets, each of the buckets having a straight configuration, the staples being crimped by the buckets so that the legs extend to or beyond the backspan.

In certain embodiments, the cartridge assembly includes an inner annular array of staples and an outer annular array of staples, and the anvil member includes an inner annular array and an outer annular array of staple forming buckets. A length of each of the staples in the inner annular array of staples can be shorter than a length of the each of the staples in the outer annular array of staples and a length of each of the staple forming buckets in the inner annular array of staple forming buckets can be shorter than a length of the each of the staple forming buckets in the outer annular array of staple forming buckets. A gap between each consecutive staple in the inner annular array of staples can be equal to a gap between each consecutive staple in the outer annular array of staples and a gap between each consecutive staple forming bucket in the inner annular array of staple forming buckets can be equal to a gap between each consecutive staple forming bucket in the outer annular array of staple forming buckets.

A gap between each consecutive staple in the inner annular array of staples can be equal to a gap between each consecutive staple in the outer annular array of staples and a gap between each consecutive staple forming bucket in the inner annular array of staple forming buckets can be equal to a gap between each consecutive staple forming bucket in the outer annular array of staple forming buckets.

In certain embodiments, a length of each of the staples in the inner and outer annular array of staples are equal to one another and a length of each of the staple forming buckets in the inner and outer annular array of staple forming buckets are equal to one another.

In another aspect of the present disclosure, a surgical stapler comprises: a tubular body portion; a cartridge assembly disposed at a distal end of the body portion for expelling inner and outer annular arrays of staples having legs and a generally bent or curved backspan, wherein a length of the backspan of the staples in the outer annular array of staples is greater than a length of the backspan of the staples in the inner annular array of staples; and an anvil member disposed at the distal end of the tubular body portion and positioned opposite the cartridge assembly to crimp the staples in tissue upon expulsion of the staples from the cartridge assembly, the anvil member having corresponding inner and outer annular arrays of staple forming buckets, each of the staple forming buckets having a straight configuration, the staples being crimped by the buckets so that the legs extend to or beyond the backspan.

In certain embodiments, a gap between each consecutive staple in the inner annular array of staples is equal to a gap between each consecutive staple in the outer annular array of staples and a gap between each consecutive staple forming bucket in the inner annular array of staple forming buckets is equal to a gap between each consecutive staple forming bucket in the outer annular array of staple forming buckets.

In another aspect of the present disclosure, a surgical stapler comprises: a tubular body portion; a cartridge assembly disposed at a distal end of the body portion for expelling a first annular array of staples, each of the staples of the first annular array of staples having a generally straight backspan; and an anvil member disposed at the distal end of the tubular body portion and positioned opposite the cartridge assembly to crimp the staples in tissue upon expulsion of the staples from the cartridge assembly, the anvil member having a corresponding first annular array of staple forming buckets, each of the buckets having a curved or bent configuration such that the annular arrays of staples are crimped beyond the generally straight backspan during formation thereof to provide a first compressive space.

The surgical stapler may have a second annular array of staples and a corresponding second annular array of staple forming buckets, wherein the second annular array of staple forming buckets includes a depth that is less than a depth of the first annular array of staple forming buckets. The formed staples of the second annular array of staples may be crimped to provide a second compressive space that is different than the first compressive space.

In another aspect, a surgical stapler comprises: a tubular body portion; a cartridge assembly disposed at a distal end of the body portion for expelling a first annular array of staples, each of the staples of the first annular array of staples having a generally angled backspan; and an anvil member disposed at the distal end of the tubular body portion and positioned opposite the cartridge assembly to clinch the staples in tissue upon expulsion of the staples from the cartridge assembly, the anvil member having a corresponding first annular array of staple forming buckets, each of the buckets configured to accommodate the generally straight configuration of the staples to facilitate formation thereof such that the annular arrays of staples are crimped beyond the generally angled backspan during formation thereof to provide a first compressive space.

BRIEF DESCRIPTION OF THE DRAWING

Various embodiments of the present disclosure are described hereinbelow with references to the drawings, wherein.

DETAILED DESCRIPTION

Figure 1:
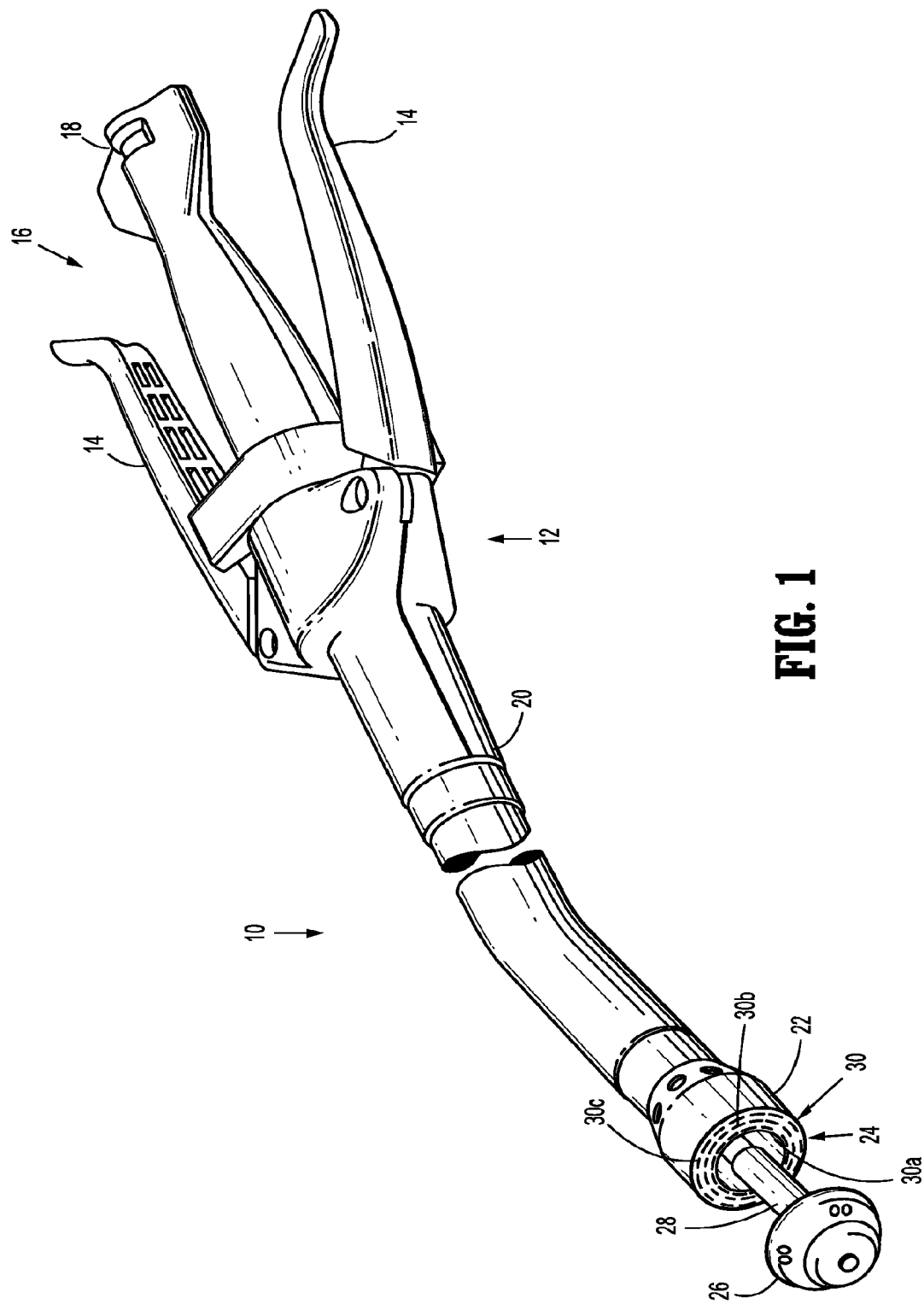
FIG. 1 is a perspective view of a surgical stapling apparatus including an anvil member and a cartridge assembly according to an embodiment of the present disclosure.
Figure 2:
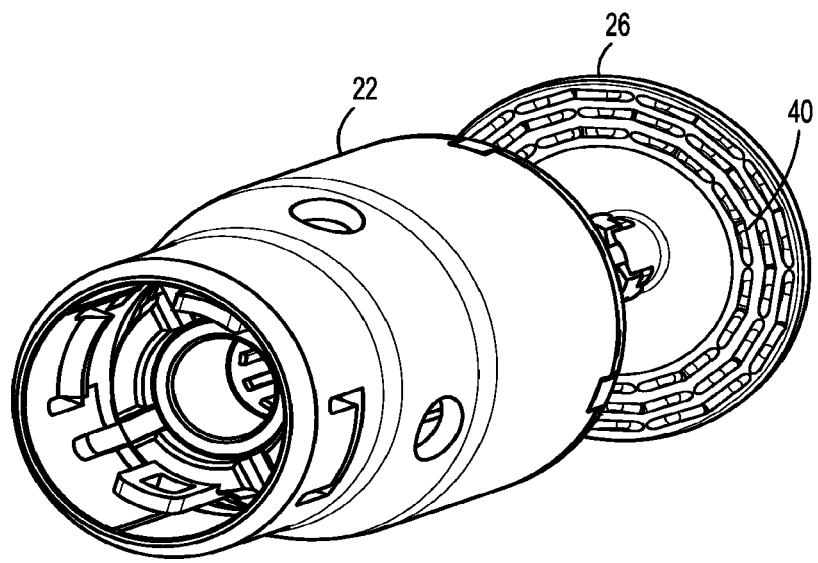
FIG. 2 is a perspective view of the anvil member and cartridge assembly depicted in FIG. 1.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to the end of a surgical instrument that is closer to the user, while the term "distal" will refer to the end of the surgical instrument that is farther from the user.

Referring now in specific detail to the drawings, in which like reference numerals identify similar or identical elements throughout the several views, FIG. 1 shows a surgical stapling apparatus 10 (apparatus 10) in accordance with an embodiment of the present disclosure. Apparatus 10 is configured to perform a circular anastomosis of a tubular organ. Briefly, apparatus 10 includes a handle assembly 12 having one or more pivotable actuating handle members 14 (two pivotable handle members 14 shown in the drawings). Apparatus 10 includes an advancing device 16 including a rotatable grip member 18 that is configured to approximate an anvil member 26 towards a cartridge assembly 22. Extending from handle assembly 12 is a tubular body portion 20 that includes a generally curved configuration. In certain embodiments, body portion 20 may also be straight and, in other embodiments, may be flexible to bend to any configuration. Body portion 20 terminates in cartridge assembly 22 that is associated with an annular array of staples 24, see FIGS. 1, 6 and 7. Anvil member 26 is positioned opposite cartridge assembly 22 and is connected to apparatus 10 by shaft 28 at connection device or structure (not explicitly shown) operably disposed within the cartridge assembly 22. For a more detailed description of the body portion 20, advancing device 16, handle assembly 12 including handle members 14 reference is made to commonly-owned U.S. Pat. No. 5,915,616 to Viola et al., filed on Oct. 10, 1997, which is incorporated in its entirety herein by reference. For example, the tubular body portion 20 can include a shaft for connection to the shaft 28 and the rotatable grip member 18 when rotated moves the shaft of the body portion 20 and approximates the anvil member 26 with the staple cartridge assembly 22. The stapling apparatus 10 further includes a pusher member, having a plurality of fingers for advancing the staples out of the cartridge assembly 22 and toward the anvil member. Movement of the pivoting actuating handle members 14 moves the pusher member to eject the staples. The handle assembly 12 includes assemblies for moving the shaft of the body portion 20 and pusher member. For example, a cam member having a helical groove receives a pin of the grip member 18 so that as the grip member is rotated, the cam member moves proximally, moving the shaft of the body portion 20. Threaded members and other means can be used to actuate the pusher member and move the anvil member 26 toward and away from the cartridge assembly 22. It is contemplated that the cartridge assembly is a removable and replaceable unit, so that the stapling apparatus 10 can be reloaded and used again.

It is also contemplated that the apparatus has a replaceable head including the cartridge assembly, anvil member and associated mechanisms. The stapling apparatus 10 can include the manually actuated handle assembly of FIG. 1 and as described above, or can include a powered actuator assembly having first and second drive members. For example, U.S. patent application Ser. No. 12/946,082, filed Nov. 15, 2010, the entire disclosure of which is hereby incorporated by reference herein, discloses a surgical device having a powered actuator assembly. Such actuator assembly can be powered by a motorized handle.

With reference to now to FIGS. 2, 6-9, anvil member 26 and cartridge assembly 22 according to an embodiment of the present disclosure is illustrated.

Figure 6:
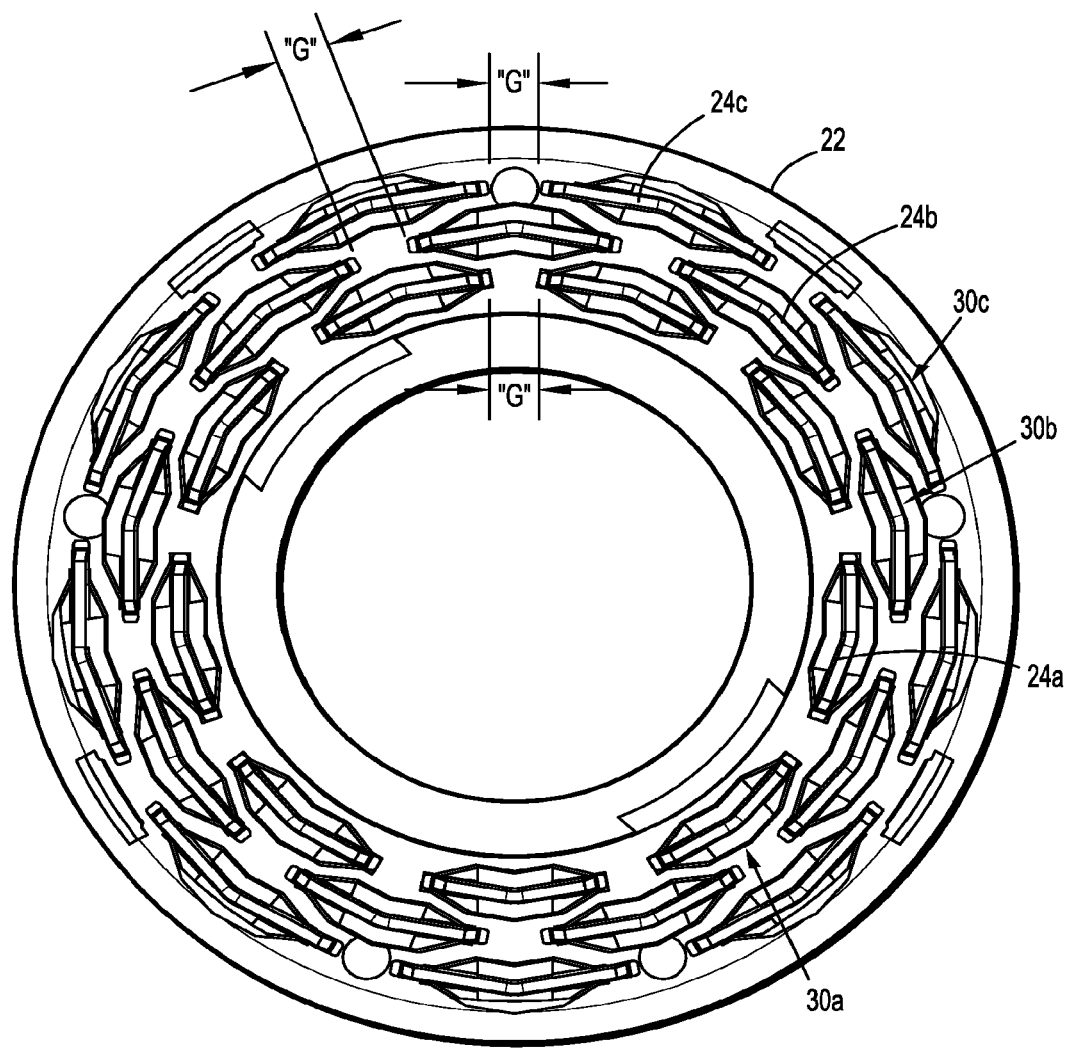
FIG. 6 is a plan view of the cartridge assembly and array of staples contained therein depicted in FIG. 1.
Figure 7:
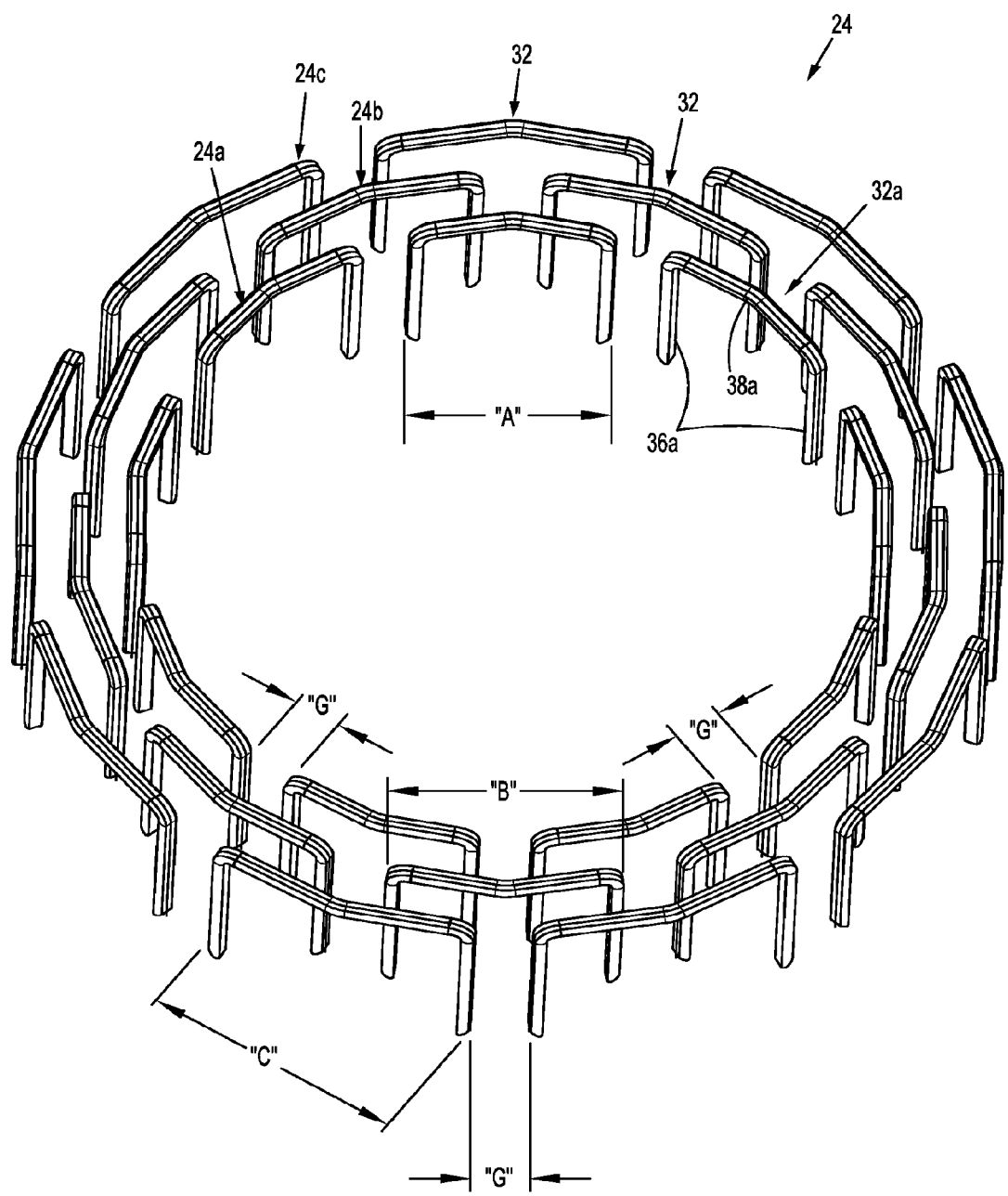
FIG. 7 is a perspective view of the array of staples depicted in FIG. 6.

Cartridge assembly 22 is configured to house a plurality of staples 24 (FIGS. 1, 6 and 7). In particular, cartridge assembly 22 includes an array of annular slots 30 (FIGS. 1 and 6) that are configured to house a corresponding annular array of staples 24 (FIGS. 6 and 7). In the illustrated embodiment, there are three annular arrays of slots 30 including an inner annular array of slots 30a, a middle annular array of slots 30b and an outer annular array of slots 30c (collectively referred to herein as slots 30 unless otherwise noted) and three corresponding annular arrays of staples including an inner annular array of staples 24a, a middle annular array of staples 24b and an outer annular array of staples 24c (collectively referred to herein as staples 24 unless otherwise noted), see FIG. 6. In certain embodiments, cartridge assembly 22 and anvil member 26 may include two annular arrays of staples and corresponding slots.

Slots 30 are aligned with a plurality of corresponding staple pushers (not explicitly shown). In certain embodiments, the staple pushers include a generally bent configuration to facilitate expelling the staples 30 from the cartridge assembly 22. In other embodiments, the staple pushers may be configured with other configurations, i.e., straight, rounded, etc.

Staples 24 may be made from any suitable biocompatible material including, but not limited to, surgical steel, shape memory alloys, polymeric materials, etc. In the illustrated embodiment, the staples 24 are made from surgical steel. In certain embodiments, it may prove advantageous to have one or more annular array of staples, e.g., inner annular array of staples 24a, made from one material and one or more annular array of staples, e.g., middle annular array of staples 24b and outer annular array of staples 24c, made from a different material.

Figure 5:
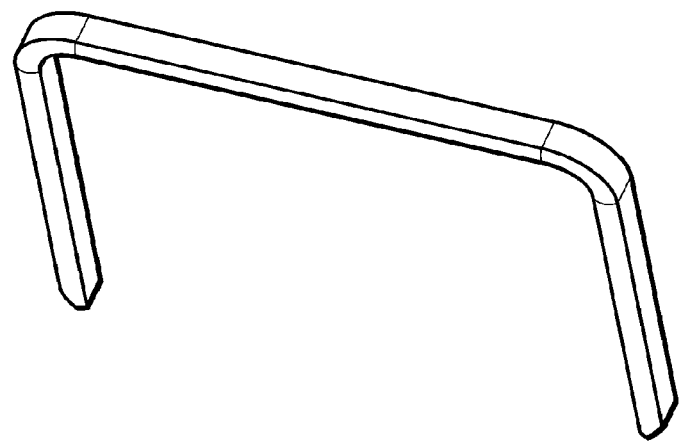
FIG. 5 is a perspective view of a prior art staple having a straight backspan.

Staples 24 are similar to conventional staples, however, unlike conventional staples (FIG. 5), staples 24 include a backspan 32 having a generally bent or angled configuration, as best seen in FIG. 7. The bent backspan of the staples 24 allows the staples to be arranged such that an equal or consistent gap distance "G" between each consecutive staple in the inner annular array of staples 24a, middle annular array of staples 24b, and outer annular array of staples 24c is achievable (FIG. 9), as described in greater detail below.

Continuing with reference to FIG. 7, the operative features of the staples 24 are described in terms of staples 24a of the inner annular array of staples 24a. Staples 24a include a pair of legs 36a having a generally pointed tip (as best seen in FIG. 7), although the tip may include other suitable configurations, e.g., blunt, flat, beveled, etc. Legs 36a extend from a backspan 32a.

Backspan 32a includes a generally bent or curved configuration, wherein a radius of curvature of the backspan 32a is greatest at a medial portion 38a (FIG. 7). The radius of curvature at the medial portion 38a may be adjusted to accommodate specific surgical procedures, specific surgical devices, a number of annular arrays of staples, a manufacturer's contemplated uses, etc. The bent backspan 32a of the staples 24a allows the staples 24a to be arranged in the inner annular array staples 24a with a minimum gap distance "G" between each consecutive staple 24a. That is, unlike conventional staples with straight backspans, the bent backspan 32a of the staple 24a is configured to follow a contour of the cartridge assembly 22 and, thus, allow a "tighter" grouping of the staples 24a (i.e., a higher density of staples) in the inner annular array of staples 24a. Moreover, a bent backspan 32b and 32c of the staples 24b and 24c, respectively, allows the lengths of the staples in these annular arrays to be larger than the lengths of the staples 24a in the annular array of staples 24a. That is, because of the bent backspans 32b and 32c of respective staples 24b and 24c, a length of the staples 24b and 24c can be increased to accommodate "overlapping" of specific gap distances "G" between consecutive staples 24a in the annular array of staples 24a. For example, and with specific reference to FIG. 7, each staple 24a in the inner annular array of staples 24a includes a length "A" and a gap between each consecutive staple 24a in the inner annular array of staples 24a is equal to gap "G." The length of staples 24b in the middle annular array of staples 24b includes a length "B" that is larger than the length "A" of the staples 24a, and a gap between each consecutive staple 24b in the middle annular array of staples 24b is equal to the gap "G" (see FIG. 7). The length of staples 24c in the outer annular array of staples 24c includes a length "C" that is larger than the lengths "A" and "B" of the respective staples 24a and 24c, and a gap between each consecutive staple 24c in the outer annular array of staples 24c is equal to the gap "G" (see FIG. 7).

As can appreciated, the "tighter" grouping of the staples 24a-24c allows the staples to "nested" and, thus, more closely packed together with respect to one another for a given cartridge assembly 22 when compared to staples with straight backspans. This "nested" configuration of the staples 24a-24c provides an increased inside diameter of staples 24a when compared to staples with straight backspans.

Figure 3:
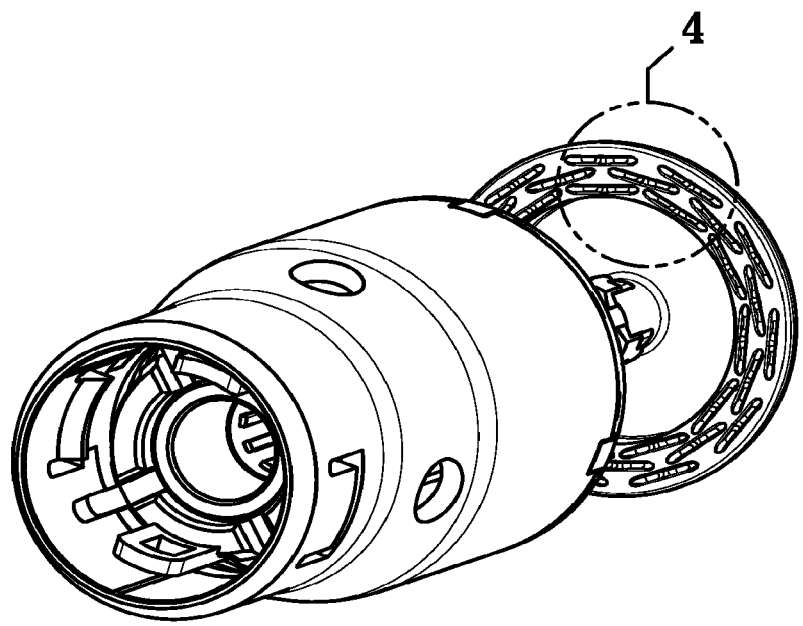
FIG. 3 is a perspective view of a prior art cartridge assembly and anvil member.
Figure 4:
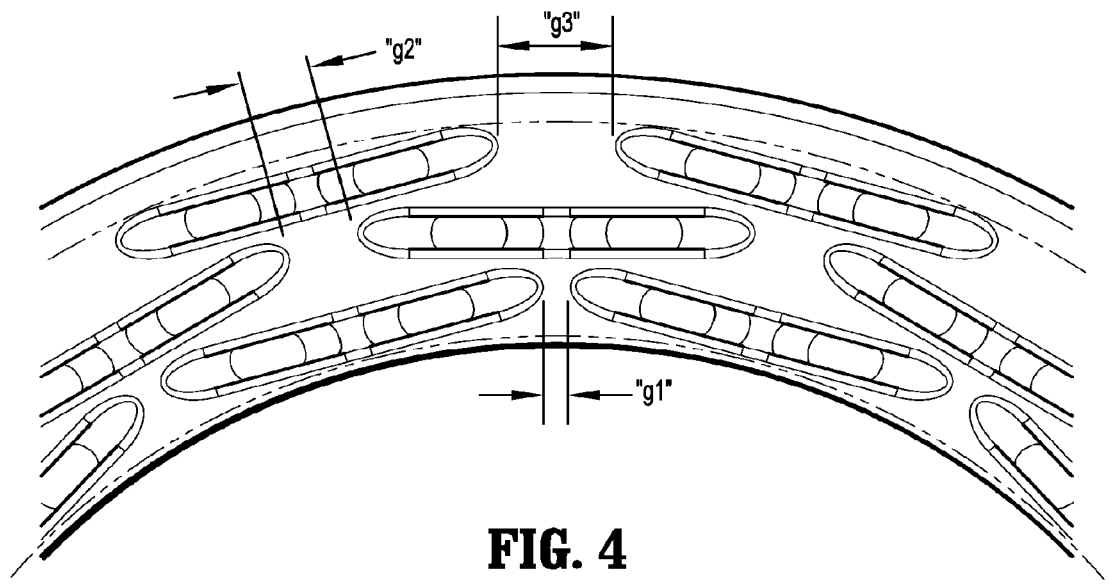
FIG. 4 is a perspective view of an enlarged area of detail depicted in FIG. 3.
Figure 8:
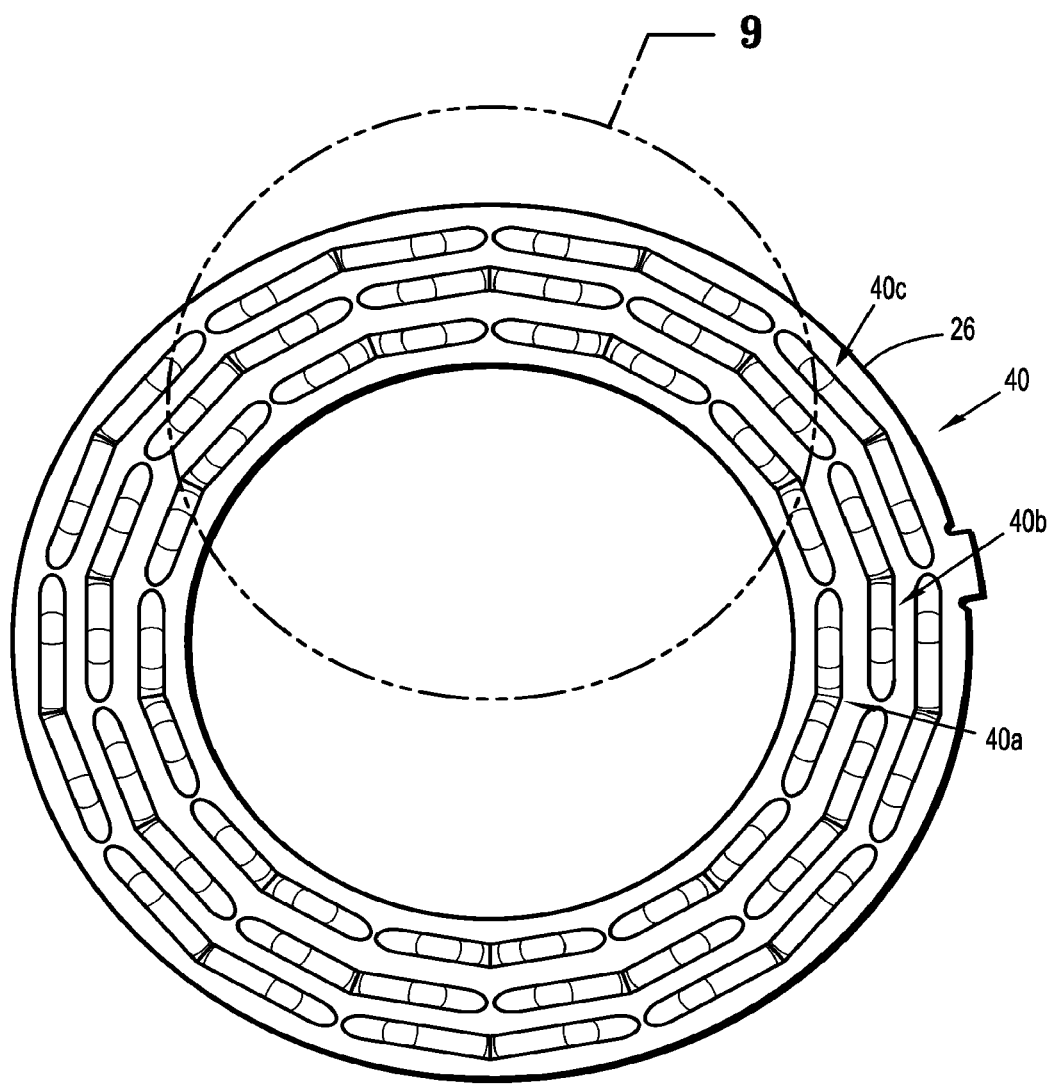
FIG. 8 is a plan view of the anvil member depicted in FIG. 2.
Figure 9:
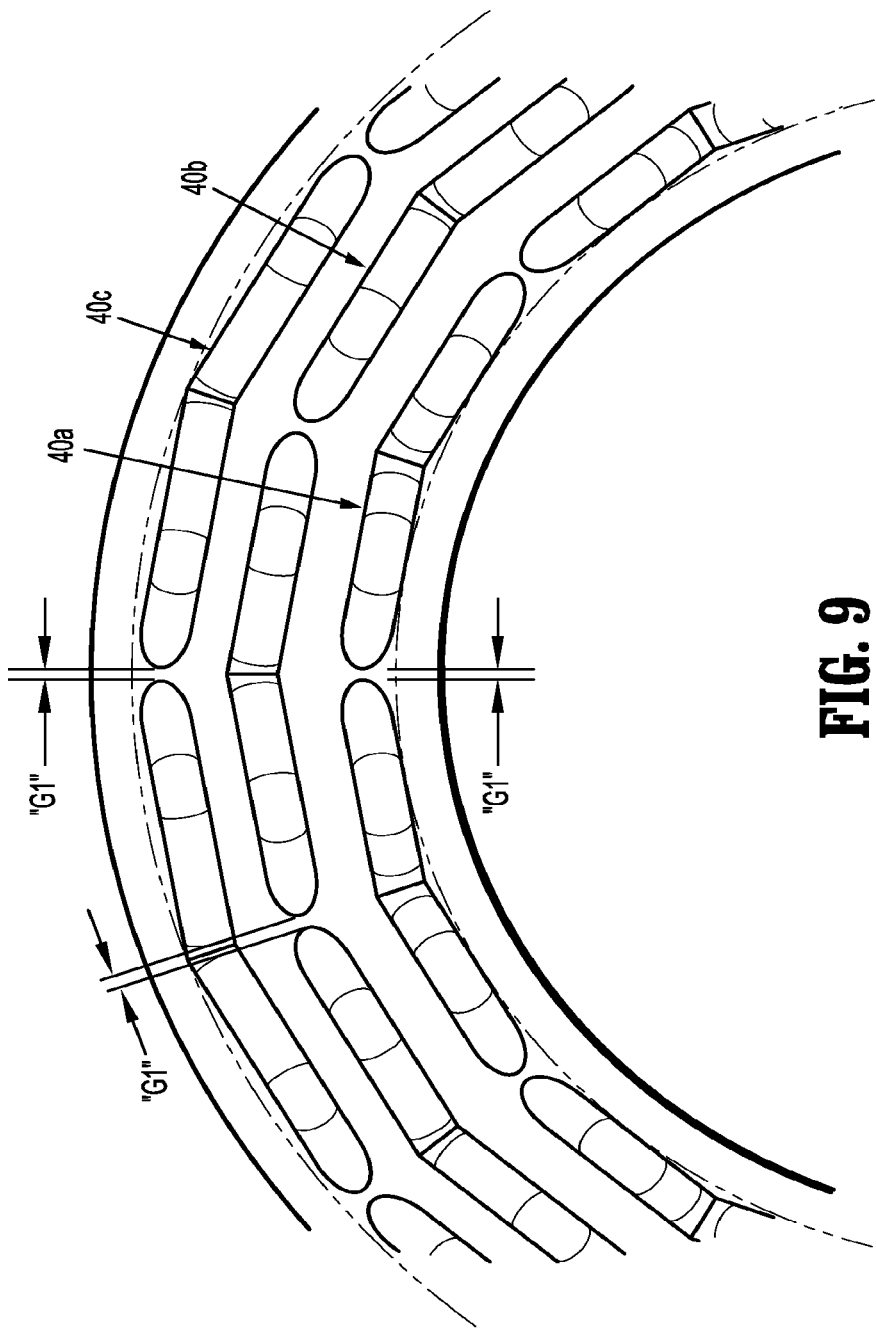
FIG. 9 is a plan view of an enlarged area of detail depicted in FIG. 8.

With reference now to FIGS. 8 and 9, anvil member 26 includes corresponding annular arrays of staple forming buckets 40 including an inner annular array of staple forming buckets 40a, a middle annular array of buckets 40b and an outer annular array of buckets 40c. Unlike conventional staple forming buckets (FIGS. 3 and 4), each of the staple forming buckets 40a, 40b and 40c are configured to accommodate the generally bent configuration of the corresponding staples 24a, 24b and 24c to facilitate formation thereof. To this end, each of the buckets 40a, 40b and 40c include a generally bent or curved configuration and is proportioned to respective staples 24a, 24b and 24c therein such that the staples 24a, 24b and 24c have a generally "B" configuration upon formation thereof. A radius of curvature of the staple forming buckets 40a, 40b and 40c is greatest at a medial portion 38a to match the radius of curvature of the corresponding staples 24a, 24b and 24c.

Continuing with reference to FIGS. 8 and 9, the dimensions of the staple forming bucket 40a in the inner annular array of staple forming buckets 40a is substantially equal to the dimensions of the corresponding staples 24a. In particular, the staple forming bucket 40a is slightly larger than the staple 24a to facilitate forming the staple 24a into the "B" formation. A gap between each consecutive staple forming bucket 40a in the inner annular array of staple forming bucket 40a is equal to gap "$G_1$." In the illustrated embodiment, the gap "$G_1$" is illustrated less than the gap "G" as a result of the staple forming bucket 40a being larger than the staple 24a. Alternatively, and in certain embodiments, the gap "$G_1$" may be equal to the gap "G." Similarly, the dimensions of the staple forming buckets 40b and 40c of the middle and outer annular arrays of staple forming buckets 40b and 40c are substantially equal to the dimensions of the corresponding staples 24b and 24c of the middle and outer annular arrays of staples 24b and 24c. The gap between each consecutive staple forming buckets 40b and 40c is equal to the gap "$G_1$" between each consecutive staple forming bucket 40a, see FIG. 9.

In use, tissue, e.g., a portion of a tubular organ, is positioned between the anvil member 26 and cartridge assembly 22. Rotatable grip 18 of the advancing device 16 is actuated to approximate the anvil member 26 towards the cartridge assembly 22. Handles 14 may be pivoted to drive or expel the staples 24 through the tissue against the anvil member 26 to complete a circular anastomosis of a tubular organ.

In accordance with the present disclosure, the annular arrays of formed staples 24a, 24b and 24c form a "tight" staple line by virtue of the consistent gap "G" between consecutive staples 24a, 24b and 24c in the inner, middle and outer annular arrays of staples 24a, 24b and 24c, and the likelihood of bleeding or leaking occurring between consecutive staples 24a, 24b and 24c in the inner, middle and outer annular arrays of staples 24a, 24b and 24c is reduced, if not eliminated. The unique bent configuration of the staples 24a, 24b and 24c and corresponding staple forming buckets 40a, 40b and 40c overcomes the aforementioned drawbacks typically associated with conventional surgical stapling devices. That is, gaps "g1," "g2," and "g3" (FIGS. 3 and 4) between consecutive staple forming buckets in respective inner, middle and outer annular arrays of conventional surgical stapling devices, increase from the inner annular array toward the outer annular array, i.e., "g1"<"g2"<"g3;" as can be appreciated, the formed staples in tissue will be spaced apart from one another at a distance that corresponds to the gap distances "g1," "g2," and "g3," of the staple forming buckets. As noted above, these "unequal" gap distances are not conducive in obtaining a "tight" staple line.

Figure 10:
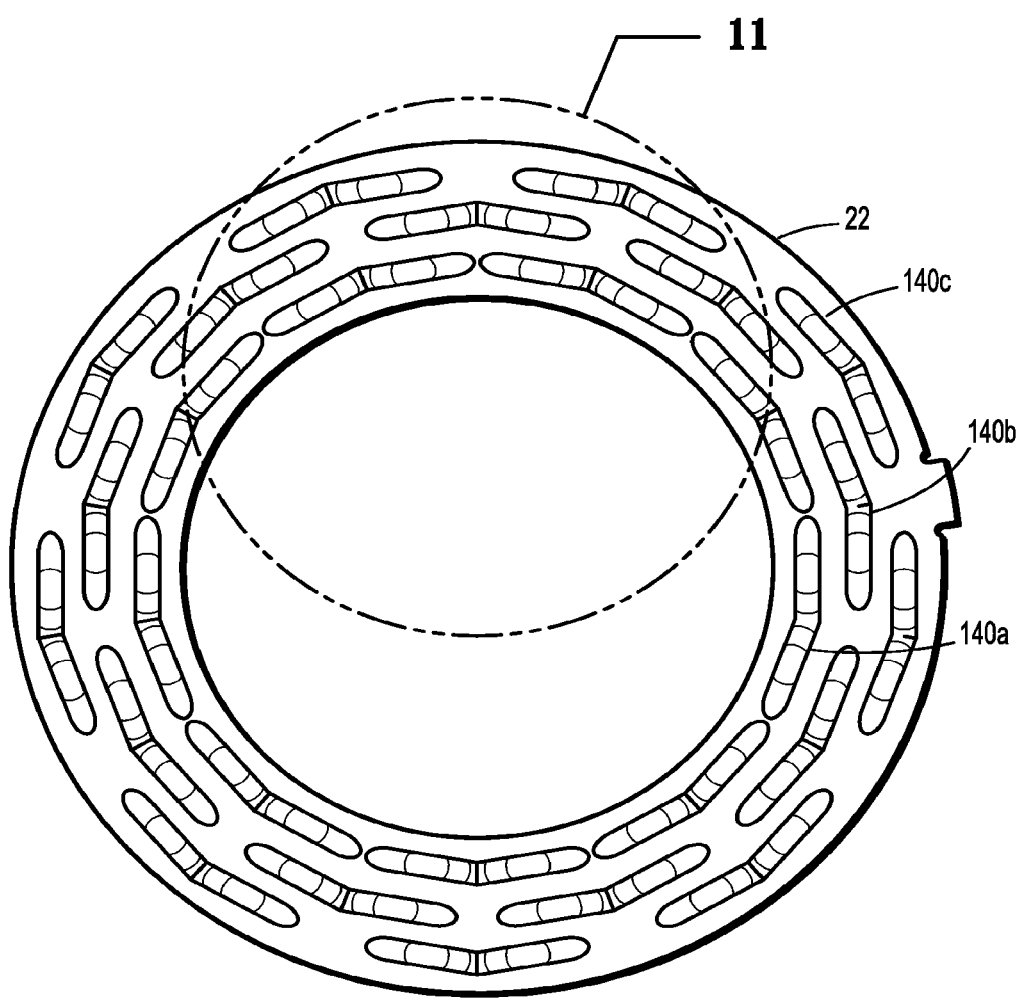
FIG. 10 is a plan view of an anvil member according to an alternate embodiment of the present disclosure.
Figure 11:
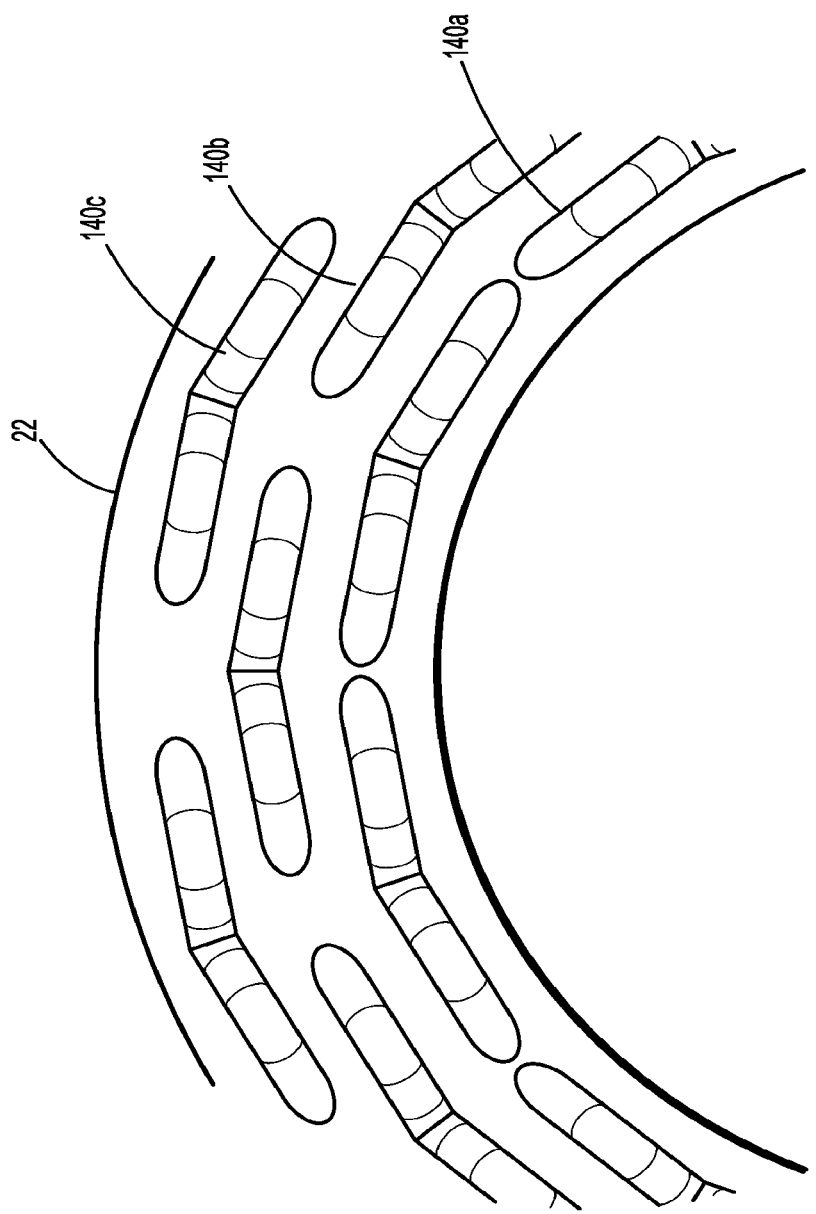
FIG. 11 is a plan view of an enlarged area of detail depicted in FIG. 10.
Figure 12:
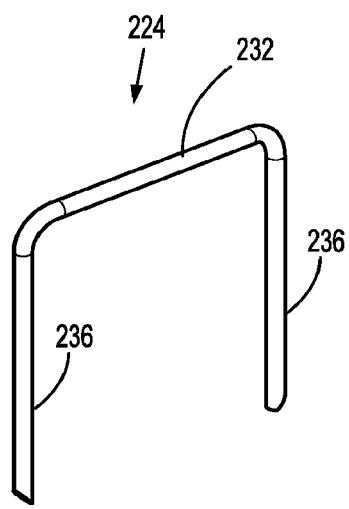
FIG. 12 is perspective view of a prior art staple.

From the foregoing and with reference to the various figure drawings, those skilled in the art will appreciate that certain modifications can also be made to the present disclosure without departing from the scope of the same. For example, while the staples 24a, 24b and 24c and corresponding staple forming buckets 40a, 40b and 40c have been described herein as having different lengths, it is within the purview of the present disclosure that the staples 24a, 24b and 24c and corresponding staple forming buckets 40a, 40b and 40c may have the same lengths (FIGS. 10 and 11). In this embodiment, the staples (not explicitly shown) and corresponding staple forming buckets 140 including inner, middle and outer annular arrays of staple forming buckets 140a-140c have the same length. In the embodiment illustrated in FIGS. 10 and 11, an equal number of staple forming buckets 140 are shown in the inner annular array of staple forming buckets 140a, middle annular array of staple forming buckets 140b and outer annular array of staple forming buckets 140c. This embodiment may prove advantageous where a "tight" staple line is not required.

In the instance where a "tight" staple line is required, however, the unique bent backspan of the staples and corresponding staple forming buckets 140b-140c allows for one or more extra staples (or larger staples) and corresponding staple forming buckets 140b-140c to be provided in the middle and outer annular arrays of staples and corresponding staple forming buckets 140b-140c. That is, for a given cartridge assembly and anvil, the geometry, e.g., bent backspan, of the staples and corresponding staple forming buckets 140b-140c follows a contour of the cartridge assembly and anvil, respectively, and, as a result thereof, allows extra staples and staple forming buckets 140b to be provided in the annular array of staple forming buckets 140b without interfering with staples and staple forming buckets 140c. And, likewise, allows extra staples and staple forming buckets 140c to be provided in the annular array of staple forming buckets 140c without interfering or extending into an outer peripheral edge of the cartridge assembly and anvil. The extra staples and corresponding staple forming buckets 140a-140c may be provided to sufficiently overlap the gaps between consecutive staples and staple forming buckets 140a-140c.

With reference to FIGS. 12-15B an alternate embodiment of the staple and staple forming buckets are illustrated designated 224 (FIG. 12) and 240 (FIGS. 13A and 13B), respectively. Only those features unique to staples 224 and staple forming buckets 240 are discussed herein.

In the embodiment illustrated in FIGS. 12-15B, staples 224 and staple forming buckets 240 may be utilized to provide formed staples with different internal spaces for compressing tissue to achieve a desired level of hemostasis and blood flow in stapled tissue segments. In one particular embodiment, for example, an inner annular row of staples 224a (staples 224a) may provide a greater compressive space (FIGS. 14A and 14B) for stapling tissue than an outer annular row of staples 224b (staples 224b), see FIGS. 15A and 15B. In other words, staples 224b in a formed configuration provide a greater compressive force to stapled tissue than the staples 224a in a formed configuration. Thus, because a pressure exerted on tissue stapled by staples 224b is greater than the pressure exerted on tissue stapled by staples 224a, the blood flow through the tissue surrounding staples 224b will be less (more restricted) than the blood flow through the tissue surrounding staples 224a, thereby further facilitating hemostasis. However, because blood flow is not completely restricted through tissue stapled by staples 224b, blood perfusion is improved and unnecessary necrosis of the stapled tissue may be prevented and/or impeded.

Staples 224a and 224b include respective staple legs 236a (FIGS. 14A-14B) and 236b (FIGS. 15A-15B) that extend from backspans 232a, 232b. In the embodiment illustrated in FIGS. 12-15B, staple legs 236a and 236b have the same length as each other, and backspans 232a, 232b include a "straight" configuration to facilitate forming staples 224a, 224b in the staple forming buckets 240a, 240b (FIGS. 13A and 13B).

Figure 13A:
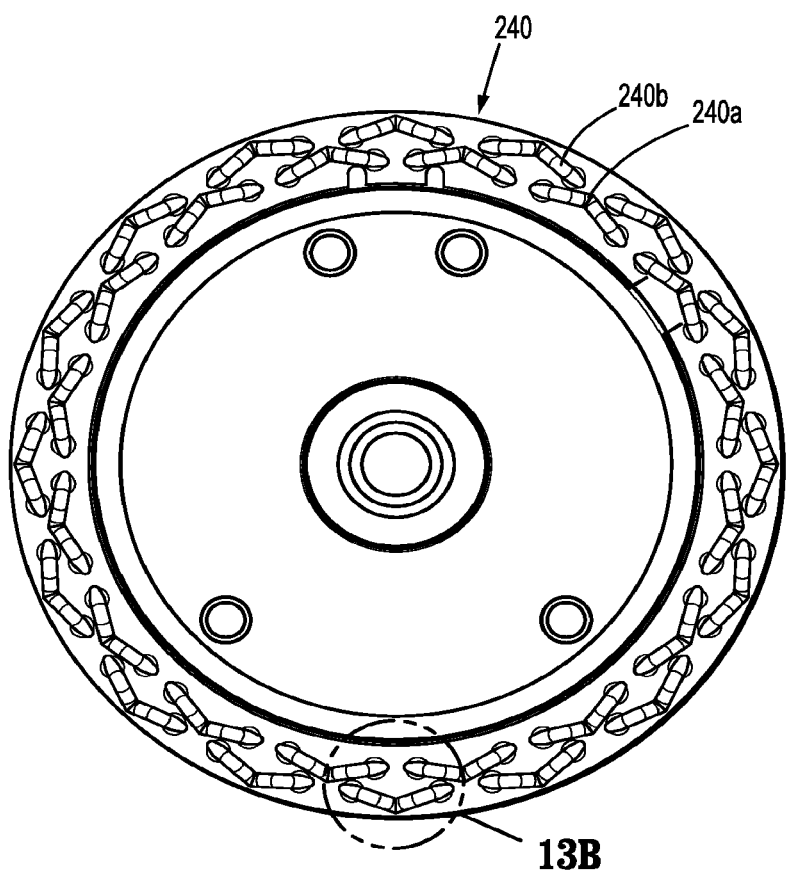
FIG. 13A is a plan view of an anvil member according to an alternate embodiment of the present disclosure.
Figure 13B:
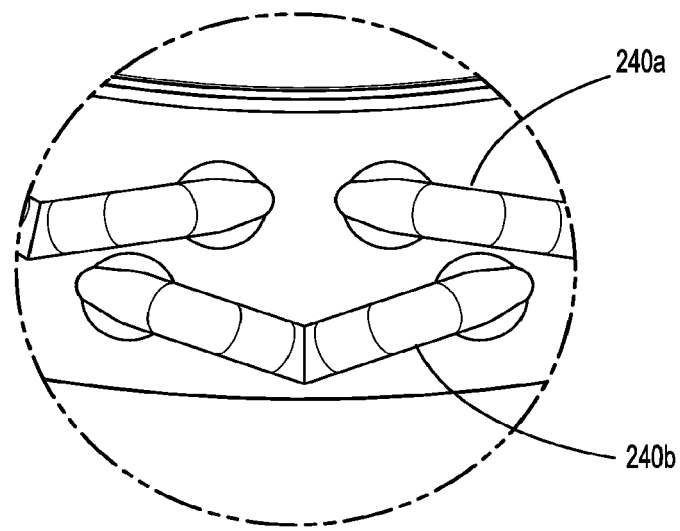
FIG. 13B is a plan view of an enlarged area of detail depicted in FIG. 13A.
Figure 14A:
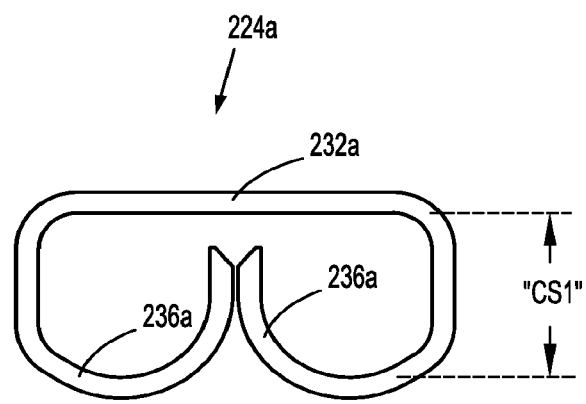
FIG. 14A is side view of the prior art staple of FIG. 12 shown in a formed configuration.
Figure 14B:
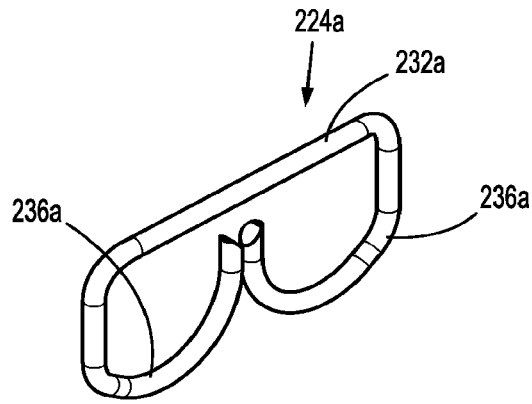
FIG. 14B is perspective view of the formed staple of FIG. 14A.
Figure 15A:
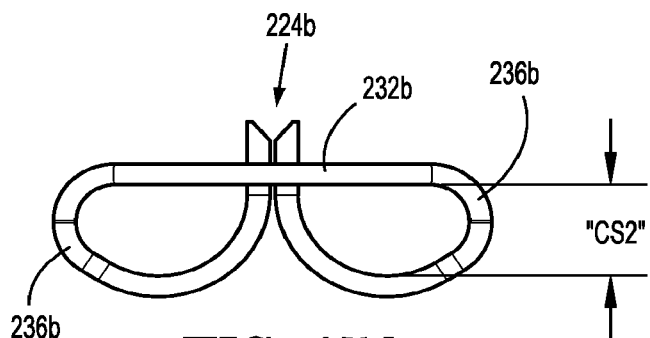
FIG. 15A is side view of the prior art staple of FIG. 12 shown in a formed configuration.
Figure 15B:
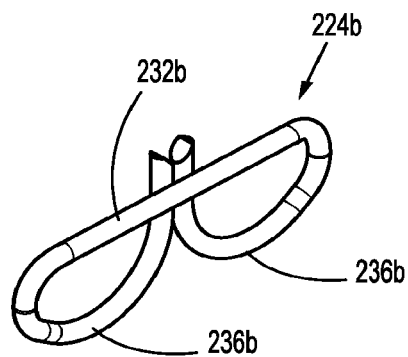
FIG. 15B is perspective view of the formed staple of FIG. 15A.

Staple forming buckets 240 are described herein in terms of inner annular row of staple forming buckets 240a (buckets 240a) and outer annular row of staple forming buckets 240b (buckets 240a), see FIGS. 13A and 13B. As can be appreciated, greater or fewer rows of buckets 240 may be utilized.

Each of buckets 240a and 240b are configured to receive corresponding staples 224a and 224b therein to form the staples 224a and 224b. Buckets 240a and 240b include an angled configuration to facilitate forming the respective staples 224a and 224b. Unlike the previously described staple forming buckets, however, buckets 240a include depth that is different from a depth of buckets 240b to facilitate forming the staples 224a and 224b with different compressive spaces. For example, and in one particular embodiment, buckets 240a include a depth that is greater than a depth of the buckets 240b to form the staples 224a with a compressive space "CS1" (FIG. 14A) that is greater than a compressive space "CS2" (FIG. 15A) of the staples 224b. Specifically, the angled buckets 240a, 240b having different depths in combination with the staples 224a, 224b having respective straight backspans 232a, 232b and legs 236a and 236b with the same length allows the staples 224a, 224b to formed with different compressive spaces, see FIGS. 14B and 15B for example. That is, this specific combination of staples 224a, 224b and buckets 240a, 240b allows staples 224b to be crimped beyond the backspan 232b (FIGS. 15A-15B) to provide a compressive space "CS2" that is less than a compressive space "CS1" provided by the staples 224a such that tissue stapled by staples 224b is under greater pressure than tissue stapled by staples 224a. In this way, the backspan does not interfere with the deformation of the legs of the staples, and the degree of crimping can be varied. The staples can be crimped by the buckets so that the legs of the staples extend to or beyond the backspan without interference from the backspan.

In certain embodiments, it may prove advantageous to have the staples 224a exert a greater pressure to stapled tissue than the staples 224b. In this embodiment, buckets 240a will include a depth that is less than a depth of the buckets 240b.

In certain embodiments, each of the staples 224a, 224b may be crimped beyond the respective backspans 232a, 232b. For example, the buckets 240a may have a depth that is configured to crimp the staples 224a beyond the backspan 232a such that the compressive space provided therefrom is greater than or less than the compressive space provided by staples 224b.

In one particular embodiment, the buckets 240a, 240b may have the same depth and the staple legs 236a, 236b may have different lengths to achieve the aforementioned compressive spaces. Those skilled in the art will appreciate the various lengths of the staple legs 236a, 236b that will be needed to achieve a specific compressive space when the staples 224a and 224b are formed.

In certain embodiments, the operation of the advancing device 16, the pusher member, or both, can be utilized to vary the degree to which the staples are deformed or crimped. For example, by approximating the anvil member more closely with the cartridge assembly, the staples are crimped with a relatively smaller internal space and the tissue is compressed to a greater degree. Alternatively, the pusher member can be further advanced, further crimping or deforming the staples. Desirably, there is an indicator on the stapling apparatus handle assembly 12 that allows the surgeon to gauge the degree to which the staples will be crimped. The variable crimp can be used in any of the embodiments disclosed herein, including embodiments in which different sized (preformation) staples are used, same sized staples are used, bent or curved backspan staples are used, and/or bent or curved staple forming buckets are used.

Figure 16A:
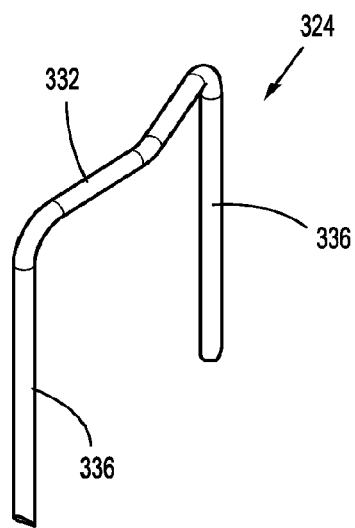
FIG. 16A is perspective view of a staple according to an alternate embodiment of the present disclosure.
Figure 16B:
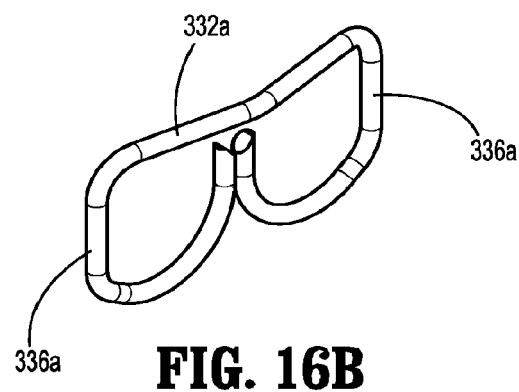
FIG. 16B is side view of the staple of FIG. 16A shown in a formed configuration.
Figure 16C:
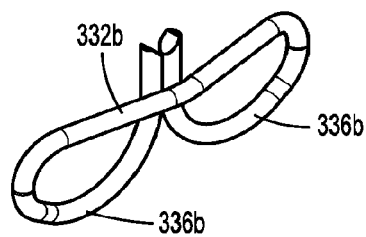
FIG. 16C is perspective view of the formed staple of FIG. 16B.

In some embodiments, such as the one illustrated in FIGS. 16A-16C, the buckets (not explicitly shown) may have a generally straight configuration and the staples 324 may include a backspan 332 having a generally angled configuration to facilitate crimping the staples 324 beyond the backspan 332. In this way, the backspan does not interfere with the deformation or crimping of the legs of the staples. The staples can be crimped by the buckets so that the legs extend to or beyond the backspan, without interference from the backspan. In one particular embodiment, for example, a formed staple 324a with legs 336a extending from an angled backspan 332a may provide a compressive space that is similar to compressive space "CS1" (FIG. 16B) and formed staple 324b with legs 336b extending from an angled backspan 332b may provide a compressive space that is similar to compressive space "CS2" (FIG. 16C). The straight configuration of the buckets can be used with any of the embodiments disclosed herein, including stapling apparatus that vary the degree of crimping or deformation of the staples, as well as embodiments in which different sized (preformation) staples are used, or same sized staples are used.

It is also contemplated that the stapling apparatus can be configured to apply three rows of staples, and that the staples can have more than one bend in the backspan, or a curved backspan that is irregular (i.e., having more than one radius), in any of the embodiments disclosed herein.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A surgical stapler, comprising:
    a tubular body portion;
    a cartridge assembly disposed at a distal end of the body portion for expelling annular arrays of staples, each of the staples of the annular arrays of staples having legs and a backspan that is curved or bent within a plane that is perpendicular to a plane defined by the legs, a length of each of the staples in an inner annular array of staples being shorter than a length of each of the staples in an outer annular array of staples, wherein at least one of the staples in the inner or outer annular array of staples has a bent or curved portion disposed between adjacent legs of adjacent staples in the other of the inner or outer annular array of staples; and an anvil member disposed at the distal end of the tubular body portion and positioned opposite the cartridge assembly to crimp the staples in tissue upon expulsion of the staples from the cartridge assembly, the anvil member having a corresponding annular array of staple forming buckets.

2. A surgical stapler according to claim 1, wherein the staples are crimped by the buckets so that the legs extend beyond the backspan.

3. A surgical stapler according to claim 1, wherein the anvil member includes an inner annular array and an outer annular array of the staple forming buckets.

4. A surgical stapler according to claim 1, further comprising a second outer array of staples.

5. A surgical stapler according to claim 3, wherein a gap between adjacent staples in the inner annular array of staples is equal to a gap between adjacent staples in the outer annular array of staples and a gap between adjacent staple forming buckets in the inner annular array of staple forming buckets is equal to a gap between adjacent staple forming buckets in the outer annular array of staple forming buckets.

6. The surgical stapler according to claim 1, wherein the backspan of each of the staples has a curved length.

7. The surgical stapler according to claim 1, wherein a length of the backspan of each of the staples in the inner annular array of staples is shorter than a length of the backspan of each of the staples in the outer annular array of staples.

8. The surgical stapler according to claim 1, wherein the backspan of each of the staples is generally bent or curved when the staples are in a pre-formed state.

9. The surgical stapler according to claim 1, wherein each bucket of the annular array of staple forming buckets has a curved or bent configuration.

10. The surgical stapler according to claim 1, wherein the length of each of the staples is defined between the legs of the staple.

11. The surgical stapler according to claim 1, wherein the bent or curved portion is a medial portion of the backspan of the at least one staple, the medial portion being disposed outside of the plane defined by the legs of the at least one staple.

12. A surgical stapler, comprising:

a tubular body portion;

a cartridge assembly disposed at a distal end of the body portion for expelling annular arrays of staples, each of the staples of the annular arrays of staples having legs and a generally bent or curved backspan, a length of each of the staples in an inner annular array of staples being shorter than a length of each of the staples in an outer annular array of staples, wherein at least one of the staples in the inner or outer annular array of staples has a bent or curved portion disposed between adjacent legs of adjacent staples in the other of the inner or outer annular array of staples; and an anvil member disposed at the distal end of the tubular body portion and positioned opposite the cartridge assembly to crimp the staples in tissue upon expulsion of the staples from the cartridge assembly, the anvil member having a corresponding annular array of staple forming buckets, wherein the staple forming buckets are configured to crimp the staples so that the legs extend beyond the backspan.

13. The surgical stapler according to claim 12, wherein the backspan of each of the staples of the annular arrays of staples is curved or bent within a plane that is perpendicular to a plane defined by the legs.

* * * * *